United States Patent [19]

Buysch et al.

[11] Patent Number: 5,231,212
[45] Date of Patent: Jul. 27, 1993

[54] PROCESS FOR THE CONTINUOUS PREPARATION OF DIALKYL CARBONATES

[75] Inventors: Hans-Josef Buysch, Krefeld; Alexander Klausener, Stolberg; Reinhard Langer, Krefeld; Franz-Josef Mais, Duesseldorf, all of Fed. Rep. of Germany

[73] Assignee: Bayer Aktiengesellschaft, Leverkusen, Fed. Rep. of Germany

[21] Appl. No.: 936,182

[22] Filed: Aug. 26, 1992

[30] Foreign Application Priority Data

Sep. 3, 1991 [DE] Fed. Rep. of Germany ....... 4129316

[51] Int. Cl.$^5$ .............................................. C07C 69/96
[52] U.S. Cl. .................................... 558/277; 558/260; 558/270; 558/274; 558/276
[58] Field of Search ......................................... 558/277

[56] References Cited

U.S. PATENT DOCUMENTS 4,181,676  1/1980  Buysch et al. ...................... 558/277
4,307,032  12/1981  Krimm et al. ...................... 558/277

FOREIGN PATENT DOCUMENTS 0000894  8/1978  European Pat. Off. .
2737265  8/1977  Fed. Rep. of Germany .
2740243  9/1977  Fed. Rep. of Germany .
2740251  9/1977  Fed. Rep. of Germany .

*Primary Examiner*—Johann Richter
*Attorney, Agent, or Firm*—Sprung Horn Kramer & Woods

[57] ABSTRACT

Dialkyl carbonates can be prepared in a continuous manner by transesterification of ethylene carbonate or propylene carbonate with alcohols in the presence of a catalyst in a column equipped with packing or baffles, by passing the reactants in countercurrent such that the ethylene carbonate or propylene carbonate are metered into the upper part of the column and the alcohol is metered into the lower part of the column and the catalyst is arranged as a fixed bed in the column or is also metered into the upper part of the column in solution or suspension, the dialkyl carbonate formed, if appropriate as a mixture with alcohol, being removed at the top of the column and the ethylene glycol or propylene glycol formed from the ethylene carbonate or propylene carbonate being removed at the foot of the column, if appropriate together with the catalyst.

13 Claims, No Drawings

PROCESS FOR THE CONTINUOUS PREPARATION OF DIALKYL CARBONATES

BACKGROUND OF THE INVENTION

1. Field of the Invention

The present invention relates to a continuous process for the preparation of dialkyl carbonates by transesterification of ethylene carbonate or propylene carbonate with $C_1$–$C_4$-alcohols in the presence of a catalyst, the starting substances being passed in countercurrent to one another.

2. Description of the Related Art

It is know that ethylene glycol carbonate and propylene glycol carbonate (glycol carbonates) can be reacted with alcohols in the presence of catalysts to give dialkyl carbonates and ethylene glycol (EG) or propylene glycol. Although these reactions can proceed with a high selectivity, the processes have a number of disadvantages in their procedure. As a rule, the transesterification proceeds relatively slowly under normal pressure, so that the use of elevated temperature, often above the boiling point of the alcohol employed, is recommended, which results in the process being carried out in pressure vessels (German Offenlegungsschrift 2 740 243 = EP 1082; and German Offenlegungsschrift 2 740 251 = EP 1083).

In this process, the reaction usually proceeds only until equilibrium is established in the transesterification reaction. After removal from the pressure container, the reaction mixture must be removed from the catalyst very quickly, for example by flash distillation, so that the starting compounds are not reformed in a reversal of the formation reaction, for example when the alcohol of low boiling point distils off. During removal from the catalyst by distillation, the glycol carbonate still in equilibrium an decompose into carbon dioxide and into polyglycols and is therefore unavailable for further transesterification, the yield being reduced, and all the by-products mentioned interfere with the working up.

However, even if this removal of the catalyst is effected satisfactorily, further distillations must still be carried out. Thus, it is first necessary to separate high-boiling components (glycols and glycol carbonates) from the low-boiling components (alcohols and dialkyl carbonates). However, distillative purification of ethylene glycol, which must have a high purity for example for the preparation of polyesters, to remove incompletely reacted ethylene glycol carbonate, which in turn is preferably employed for the preparation of dialkyl carbonates, is not possible without restriction since both compounds form an azeotrope. A similar difficulty is found when methanol, which is the preferred alcoholic component, has to be separated off from the dimethyl carbonate (DMC) formed. These compounds also form an azeotrope, which can be distilled into its separate components only in a cumbersome manner (EP 894 and literature cited therein).

SUMMARY OF THE INVENTION

In spite of diverse attempts at a solution, there was therefore an urgent need for the various difficulties mentioned to be effectively overcome. It has now been found, surprisingly, that the disadvantages mentioned in the transesterification of glycol carbonates with alcohols to give dialkyl carbonates can be eliminated if the transesterification is carried out in a column with the starting substances in countercurrent to one another; this process can be carried out under unexpectedly mild conditions.

The invention therefore relates to a process for the preparation of dialkyl carbonates of the formula $$(R^1O)_2CO \qquad (I)$$

in which $R^1$ denotes straight-chain or branched $C_1$–$C_4$-alkyl, by transesterification of ethylene carbonate or propylene carbonate with 3–30 mol, preferably 4–20 mol, particularly preferably 6–16 mol, of alcohols of the formula $$R^1OH \qquad (II)$$

in which $R^1$ has the above meaning, per mole of ethylene carbonate or propylene carbonate in the presence of catalysts, which is characterised in that the transesterification is carried out in a column equipped with packing or baffles at temperatures in the range of 60°–160° C., preferably 60°–150° C., particularly preferably 65°–130° C., and the reactants are passed in countercurrent such that the ethylene carbonate or propylene carbonate are metered into the upper part of the column and the alcohol is metered into the lower part of the column and the catalyst is arranged as a fixed bed in the column or is also metered into the upper part of the column in solution or suspension, the dialkyl carbonate formed, if appropriate as a mixture with alcohol, being removed at the top of the column and the ethylene glycol or propylene glycol formed from the ethylene carbonate or propylene carbonate being removed at the foot of the column, if appropriate together with the catalyst.

DETAILED DESCRIPTION OF THE INVENTION

In spite of the mild conditions, complete transesterification of the glycol carbonate to the dialkyl carbonate is achieved in this process, so that first of all the distillation of the glycol carbonate azeotrope into its separate components is dispensed with, since the glycol can already be removed at the foot of the column in a state free from glycol carbonate. The otherwise customary rapid separation of the reaction mixture from the catalyst is consequently superfluous, since the dialkyl carbonates are removed at the top of the column and are thus separated from the glycol and from the catalyst, and reversal of the reaction to give the starting substances is no longer possible. Moreover, in the case of a transesterification with methanol, which is preferably employed, as the alcohol, the column can be operated so that not only the expected azeotrope of methanol (about 70%) and dimethyl carbonate (about 30%) but also a mixture which contains considerably more dimethyl carbonate than corresponds to the azeotrope is obtained at the top of the column. In the case of methanol, it is therefore even possible to carry out the transesterification such that instead of pure methanol, mixtures of methanol and dimethyl carbonate, which may be obtained in other processes, are employed as the starting material in the transesterification according to the invention with glycol carbonate without a prior difficult separation. This is also possible of course when alcohols other than methanol are used. As a result of being able to use mixtures of alcohols and dialkyl carbonates instead of the pure alcohols for the transesterification, the often difficult and energy-intensive separation of the mixtures, a predominant number of which are azeotropes, is no longer necessary. The alcohol and the dialkyl carbonate in such mixtures have the same alkyl radical, which means that undesirable, complicated reaction mixtures having different alkyl radicals are avoided.

The solution to the object is distinguished by its simplicity and its straightforwardness.

In the simplest case, the column to be employed is an isothermally heated tube filled with the customary packing to be used for distillations, into the top of which the catalyst solution and the glycol carbonate are introduced. The alcohol to be used is sent from the bottom in vapour form in countercurrent to this mixture.

The transesterification steps proceed surprisingly rapidly in the tube, so that considerable amounts of dialkyl carbonate pass over at the top even in a relatively short column of this simple design.

However, the column can also comprise, at the lower end, a stripping part which operates at a higher temperature and in which substantial to complete separation of the alcohol from the glycol trickling down, and recycling into the transesterification region of the column takes place.

The column can furthermore have, in the upper part, a rectifying part which operates at a lower temperature, in order to bring the separation of gaseous alcohol and dialkyl carbonate from higher-boiling components, such as, for example, glycol and glycol carbonate, to completion and in this way to remove a high-strength or pure mixture of alcohol and dialkyl carbonate at the column top.

Energy can be supplied via the alcohol introduced into the column in vapor form and/or via the bottom evaporator. The alcohol may also be metered in in liquid form, ion which case energy must be supplied via the bottom evaporate. In the first case, a widening of the column diameter in the middle part of the column, in which the majority of the transesterification proceeds, to four times that of the other parts may be of advantage. In the second case, the evaporation enthalpy for the alcohol must be transported through the stripping part and leads to a high loading with gas and liquid here. This results in a widening of the column in the stripping part in order to guarantee the separations envisaged in that part. The widening and length of the stripping part depend on the column baffles chosen in the stripping part, and these can be designed by the expert.

Since two molecules of alcohol are replaced by one molecule of dialkyl carbonate in the course of the transesterification in the gas phase, a reduction in cross-section by not more than a factor of 2 may be advantageous to keep the speed of the gas constant in the middle part of the column.

The column can thus either be heated isothermally or, preferably, be equipped with one or more temperature zones which differ from the main part, resulting in a temperature gradient with values which increase from the top downwards.

The packing or ordered fillings to be used are those which are customary per se for distillations, such as are described, for example, in Ullmanns's Encyclopadie der Techn. Chemie (Ullmann's Encyclopaedia of Industrial Chemistry), 4th Edition, Volume 2, page 528 et seq., or in the company literature of the apparatus engineering companies in question. Examples which may be mentioned are: Raschig or Pall rings, Berl-, Intalex- or torus-saddles, and interpacking bodies of various materials, such as glass, stoneware, procelain, carbon, high-grade steel or plastic, which can be processed in a woven fabric- or mesh-like manner, especially if metal is used. Packing and ordered fillings which have a large surface area and good wetting properties as well as an adequate residence time of the liquid are preferred. These are, for example, Pall- and Novolax-rings, Berl-saddles, BX-packing, Montz-Pak, Mellapak, Melladur, Kerapak and CY-packings.

However, not only packed columns but also those having fixed baffles are suitable for the process according to the invention. Of these, those having bubble or valve trays with high residence times coupled with a good mass transfer are preferred.

However, other tray columns are also generally suitable, for example those having perforated, bubble, valve, tunnel and centrifugal trays, which can in turn be present in various embodiments.

The column is operated such that a solution of the catalyst in the glycol carbonate employed, or also in the glycol on which this is based or also in the alcohol to be employed or also in another suitable inert solvent foreign to the system is metered into the upper half, preferably into the upper third. In the case where a catalyst which is insoluble in the reactants is employed, this can also be employed as a mixture with the packing mentioned or as a heap poured onto the column trays installed. The glycol carbonate is likewise introduced into the upper region, preferably into the upper third of the column; it preferably has a temperature the same as that prevailing at this point in the column. The alcohol, as a rule in vapour form, is metered into the lower half of the column, preferably above any stripping zone present.

The dialkyl carbonate is removed at the top of the column, preferably after passing through a rectifying zone, and is condensed. In general, it still contains portions of the alcohol in the system. A glycol which is of high-percent strength if the conditions have been set carefully is discharged from the bottom of the column, and can be separated from the catalyst and impurities in a purifying distillation.

The molar ration in the column varies from 3–30 mol, preferably 4–20 mol, particularly preferably 6–16 mol, of alcohol per mol of ethylene carbonate or propylene carbonate.

The temperature in the column is 60°–160° C., preferably 60°–150° C., particularly preferably 65°–130° C. A temperature gradient which is to be applied in a preferred manner lies in the stated temperature range and rises from the top of the column to the bottom of the column.

As a rule, the reaction of the process according to the invention is carried out under normal pressure. However, it is also possible to carry out the reaction under a slightly increased pressure of up to about 3 bar, preferably up to 2 bar, or under a reduced pressure of down to 50 mbar, preferably down to 100 mbar, particularly preferably down to 200 mbar. In a manner known to the expert, by deviating from normal pressure it may become possible to influence the azeotrope to be removed, for example, at the top.

The space/time loading of the column is 0.1–3 g of the total amount of reaction participants per ml of effective column volume per hour, preferably 0.2–2.5 g/ml/hour, particularly preferably 0.3–2.0 g/ml/hour;

the effective column volume here is that of the packing or the volume in which fixed baffles are located. Catalysts which are suitable for the process according to the invention are known in the literature.

Such catalysts are, for example, hydrides, oxides, hydroxides, alcoholates, amides or salts of alkali metals, such as lithium, sodium, potassium rubidium and caesium, preferably of lithium, sodium and potassium, particularly preferably of sodium and potassium (U.S. Pat. No. 3,642,858, U.S. Pat. No. 3,803,201 and EP 1082). In the case where the alcoholates are employed, according to the invention these can also be formed in situ by using the elemental alkali metals and the alcohol to be reacted according to the invention. Salts of the alkali metals can be those of organic or inorganic acids, such as of acetic acid, propionic acid, butyric acid, benzoic acid, stearic acid or carbonic acid (carbonates or bicarbonates), of hydrochloric acid, hydrobromic or hydriodic acid, nitric acid, sulphuric acid, hydrofluoric acid, phosphoric acid, hydrocyanic acid, thiocyanic acid, boric acid, stannic acid, $C_1$–$C_4$-stannonic acids or antimony acids. Preferred possible compounds of the alkali metals are the oxides, hydroxides, alcoholates, acetates, propionates, benzoates, carbonates and bicarbonates, and hydroxides, alcoholates, acetates, benzoates or carbonates are particularly preferably employed.

Such alkali metal compounds (formed in situ, in appropriate, from the free alkali metals) are employed in amounts of 0.001 to 2% by weight, preferably 0.005 to 0.9% by weight, particularly preferably 0.01 to 0.5% by weight, based on the reaction mixture to be reacted.

It is possible, according to the invention, to add substances which, if appropriate, complex such alkali metal compounds (EP 274 953). Examples which may be mentioned are crown ethers, such as dibenzo-18-crown-6, polyethylene glycols or bicyclic nitrogen-containing cryptands.

Such complexing agents are employed in amounts of 0.1 to 200 mol %, preferably 1 to 100 mol %, based on the alkali metal compound.

Suitable catalysts for the process according to the invention are furthermore thallium-I and thallium-III compounds, such as the oxides, hydroxides, carbonates, acetates, bromides, chlorides, fluorides, formates, nitrates, cyanates, stearates, naphthenates, benzoates, cyclohexylphosphonates and hexahydrobenzoates, cyclopentadienylthallium, thallium methylate and thallium ethylate, preferably Tl-(I) oxide, Tl-(I) hydroxide, Tl-(I) carbonate, Tl-(I) acetate, Tl-(III) acetate, Tl-(I) fluoride, Tl-(I) formate, Tl-(I) nitrate, Tl-(I) naphthenate and Tl-(I) methylate (EP 1083). The amounts of thallium catalyst are not particularly critical. They are in general 0.0001–10% by weight, preferably 0.001–1% by weight, based on the total reaction mixture.

Nitrogen-containing bases can furthermore be employed as catalysts in the process according to the invention (U.S. Pat. No. 4,062,884). Examples which may be mentioned are secondary or tertiary amines, such as triethylamine, tributylamine, methyldibenzylamine, dimethylcyclohexylamine and the like.

The amounts of nitrogen-containing bases employed according to the invention are from 0.01 to 10% by weight, preferably from 0.1 to 5% by weight, particularly preferably from 0.1 to 1% by weight, based on the total reaction mixture.

Heterogeneous catalyst systems can furthermore be employed in the process according to the invention (U.S. Pat. No. 4,062,884, U.S. Pat. No. 4,691,041, JA 6/3238 043 and EP 298 167). Such systems are, for example, ion exchanger resins with functional groups from tertiary amines, quaternary ammonium groups, examples of counter-ions which may be mentioned being hydroxide, chloride or hydrogen sulphate, sulphonic acid groups or carboxyl groups, for both of which hydrogen, alkali metals or alkaline earth metals may be mentioned as examples of counter-ions. These functional groups can be bonded to the polymer either directly or via inert chains. Alkali metal silicates or alkaline earth metal silicates, impregnated on silicon dioxide supports, and ammonium exchanged zeolites may furthermore be mentioned.

According to the invention, these heterogeneous catalysts are preferably employed in stationary form, but it is also possible for them to be used, for example, as a fine powder in suspension. In the stationary form, the catalysts can be employed, for example, instead of the packing described or as a mixture with this.

Catalysts which can furthermore be employed according to the invention are compounds from the group comprising phosphines, stibines, arsines and divalent sulphur and selenium compounds as well as onium salts thereof (EP 180 387 and U.S. Pat. No. 4,734,518). The following may be mentioned as examples: tributylphosphine, triphenylphosphine, diphenylphosphine, 1,3-bis-(diphenylphosphino)propane, triphenylarsine, trimethylarsine, tributyarsine, 1,2-bis-(diphenylarsino)ethane, triphenylstibine, diphenyl sulphide, diphenyl disulphide, diphenyl selenide, tetraphenylphosphonium halide (Cl, Br or I), tetraphenylarsonium halide (Cl, Br or I), triphenylsulphonium halide (Cl or Br) and the like.

The amounts of this catalyst group employed according to the invention are in the range from 0.1 to 10% by weight, preferably from 0.1 to 5% by weight, particularly preferably in the range from 0.1 to 2% by weight, based on the total reaction mixture.

Complexes or salts of tin, titanium or zirconium can furthermore be employed according to the invention (U.S. Pat. No. 4,661,609). Examples of such system s are butylstannone acid, tin methoxide, dimethyltin, dibutyltin oxide, dibutyltin dilaurate, tributyltin hydride, tributyltin chloride, tin(II) ethylhexanoates, zirconium alkoxides (methyl, ethyl or butyl), zirconium (IV) halides (F, Cl, Br or I), zirconium nitrates, zirconium acetylacetonate, titanium alkoxides (methyl, ethyl or isopropyl), titanium acetate, titanium acetylacetonate and the like.

The amounts which can be employed according to the invention are 0.1 to 10% by weight, preferably 1 to 5% by weight, based on the total mixture.

Bifunctional catalysts of the formula

$$[A_aX_b]_m\cdot[B_cY_d]_n \tag{III}$$

can furthermore be employed in the process according to the invention. In these bifunctional catalysts, the molar ratio of the two components in square brackets is expressed by the indices m and n. These indices can assume, independently of one another, values of 0.001–1, preferably 0.01–1, particularly preferably 0.05–1 and especially preferably 0.1–1. Within the square brackets are neutral salts of in each case one cation and one anion. The indices a and b independently of one another represent integers from 1–5; the indices c and d independently of one another denote integers from 1–3, where the valency requirements of the cations and anions for the formation of such neutral salts are to be met. Furthermore, in (III), A denotes the cation of a metal which belongs to the third period and group IIa, to the fourth period and group IIa, IVa-VIIIa, Ib or IIb, to the fifth period and group IIa, IVa-VIIa, IIb or IVb or to the sixth period and group IIa-VIa of the Periodic Table of the Elements in the short-period form.

The expert can see the metals suitable for cation A from the usual presentations of the Periodic Table of the Elements (Mendeleev) in the short-period form. A is preferably the cation of one of the metals Mg, Ca, Sr, Ba, Zn, Cu, Mn, Co, Ni, Fe, Cr, Mo, W, Ti, Zr, Sn, Hf, V or Ta, preferably the cation of one of the metals Mg, Ca, Zn, Co, Ni, Mn, Cu or Sn. In addition to the non-complexed cations of the metals mentioned, cationic oxo complexes of the metals mentioned are also possible, such as, for example, titanyl $TiO^{++}$ and chromyl $CrO_2^{++}$.

The anion X belonging to the cation A is that of an inorganic or organic acid. Such an inorganic or organic acid can be monobasic or dibasic or tribasic. Such acids and their anions are known to the expert. Examples of anions of monobasic inorganic or organic acids are: fluoride, bromide, chloride, iodide, nitrate, the anion of an alkanecarboxylic acid having 1-18 C atoms and benzoate; examples of anions of dibasic inorganic or organic acids are: sulphate, oxalate, succinate, fumarate, maleate, phthalate and others; examples of tribasic inorganic or organic anions are: phosphate or citrate. Preferred anions X in the catalyst of the formula (III) are: fluoride, chloride, bromide, iodide, sulphate, nitrate, phosphate, formate, acetate, propionate, oxalate, butyrate, citrate, succinate, fumarate, maleate, benzoate, phthalate, decanoate, stearate, palmitate and laurate. Particularly preferred anions X are: chloride, bromide, iodide, acetate, laurate, stearate, palmitate, decanoate, nitrate and sulphate.

A suitable cation B in the catalysts of the formula (III) is one from the group comprising alkali metal cations or alkaline earth metal cations, quaternary ammonium, phosphonium, arsonium or stibonium cations and ternary sulphonium cations.

Alkali and alkaline earth metal cations which may be mentioned here are: the lithium, sodium, potassium, rubidium, caesium, magnesium, calcium, strontium and barium cation, preferably the alkali metal cations mentioned, particularly preferably the sodium and the potassium cation.

Suitable cations B are preferably those of the formulae:

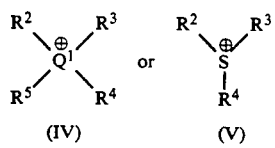

wherein $Q^1$ represents N, P, As or Sb and $R^2$, $R^3$, $R^4$ and $R^5$ independently of one another are straight-chain or branched $C_1-C_{18}$-alkyl or $C_7-C_{12}$-aralkyl, and one of the radicals $R^2-R^5$ can also be $C_6-C_{12}$-aryl.

B is particularly preferably a cation of the formula

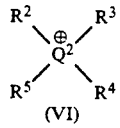

wherein $Q^2$ represents N or P, preferably N.

In the context of the formulae (IV) and (VI), the radicals $R^{12}$, $R^{13}$, $R^{14}$ and $R^{15}$, which independently of one another denote straight-chain or branched $C_1-C_{12}$-alkyl or $C_7-C_8$-aralkyl, and one of the radicals $R^{12}$ to $R^{15}$ can also be phenyl, especially preferably replace the radicals $R^2$, $R^3$, $R^4$ and $R^5$ respectively. Furthermore, the radicals $R^{22}$, $R^{23}$, $R^{24}$ and $R^{25}$, which independently of one another denote $C_1-C_8$-alkyl or benzyl, and one of the radicals $R^{22}$ to $R^{25}$ can also be phenyl, especially preferably replace the radicals $R^{12}$, $R^{13}$, $R^{14}$ and $R^{15}$ respectively.

Straight-chain or branched $C_1-C_{18}$-alkyl is, for example, methyl, ethyl, propyl, isopropyl, butyl, isobutyl, hexyl, oxtyl, dodecyl, hexadecyl or octadecyl. Preferred alkyl has 1-12 C atoms, and particularly preferred alkyl has 1-8 C atoms.

$C_7-C_{12}$-Aralkyl is, for example, benzyl, phenylethyl, phenylprophyl, naphthylmethyl or naphthyl-ethyl; preferred aralkyl is benzyl or phenylethyl, and especially preferred aralkyl is benzyl.

$C_6-C_{12}$-Aryl is, for example, phenyl, naphthyl or biphenylyl, preferably phenyl.

The anion Y in the catalyst of the formula (III) is a halide ion, such as fluoride, chloride, bromide or iodide, preferably bromide or iodide, particularly preferably iodide. However, it can also have the meaning of other anions mentioned under X, if the anion X, in the specific case, is bromide or iodide.

The bifunctional catalyst of the formula (III) is employed in an amount of 0.005-5% by weight, preferably 0.01-3% by weight, particularly preferably 0.01-1% by weight, based on the total transesterification mixture.

These amounts of catalyst in some cases differ from the amounts mentioned in the literature. It is particularly surprising that relatively high concentrations of the active catalysts based on alkali metal compounds can be employed in the process according to the invention without the evolutions of $CO_2$, which reduce the yield and impede the reaction procedure, and the formation of polyols occuring, as is known, for example, from German Offenlegungsschrift 2 740 243, in the literature cited therein and from German Offenlegungsschrift 2 740 251.

This is also a surprising feature of the process according to the invention.

EXAMPLES 1-7

A solution of the catalyst KOH in ethylene glycol and the starting substance ethylene glycol carbonate were metered separately, about 10 cm below the upper end of the column, into an isothermally thermostatically controlled column packed with Raschig rings of glass and having a length of 250 cm and a diameter of 30 mm. Methanol in vapour form, which was fed in as a vapour about 30 cm above the lower end of the column, was passed in countercurrent to this stream. A mixture of methanol and dimethyl carbonate was removed at the top of the column, which operated without a rectifying part, and ethylene glycol, which, where appropriate, still contained minor amounts of ethylene glycol carbonate and alcohol, was removed at the lower end, which had no stripping part.

The following Table 1 shows some examples of the transesterification process according to the invention and the results thereof. These were determined after constant conditions and ratios had been established in the column. Since neither a stripping nor a rectifying part were present, the bottom product still contained methanol and, where appropriate, small amounts of dimethyl carbonate, and the distillate still contained traces of ethylene glycol or ethylene glycol carbonate.

EXAMPLE 8

The process of Examples 1 to 7 was repeated, and instead of methanol, a stream of ethanol in vapour form was fed in about 30 cm above the lower end of the column. The result is shown in the following Table 2.

81.0% of EG, 18.9% of MeOH and 0.1% of EGC was discharged from the bottom.

EXAMPLE 10

When 88 g of EGC, 240 g of MEOH and 0.12 g of KOH, dissolved in 6 g of EG, were metered per hour into the column from Example 9, a top product of 60.6% of MeOH and 39.4% of DMC and a bottom product of 71.5% of EG, 21.8% of MeOH and 5.8% of EGC were obtained in the stationary state.

When the temperature in the stripping part was increased by 10°, the content of EGC in the bottom product was reduced to 0.5%.

These examples first of all shown how surprisingly smoothly and rapidly the transesterification proceeds with more than 99% selectivity under mild conditions of 70°–100° without applying pressure (in this context, compare Example 9 of EP 1082 or Example 6 and the comparison examples of EP 1083 with the present ex-

TABLE 1

| | | | | | Examples 1-7 | | | | | |
| | | | | | Distillate[1] | | | Bottom product[2] | | |
| No. | EGC g/h | Cat. g/h | MeOH g/h | Temp. °C. | g/h | % of MeOH | % of DMC | g/h | % of EG | % of EGC | % of MeOH |
| --- | --- | --- | --- | --- | --- | --- | --- | --- | --- | --- | --- |
| 1 | 101 | 0.7 | 330 | 70 | 302 | 64.9 | 34.4 | 131 | 53.5 | 0.3 | 45.5 |
| 2 | 202 | 1.4 | 660 | 80 | 599 | 66.9 | 32.1 | 259 | 53.3 | 1.2 | 44.2 |
| 3 | 195 | 1.4 | 970 | 100 | 735 | 73.3 | 25.6 | 427 | 30.4 | 4.5 | 63.2 |
| 4 | 170 | 0.7 | 660 | 70 | 457 | 62.6 | 36.9 | 366 | 33.2 | 1.7 | 63.7 |
| 5 | 250 | 1.4 | 1050 azeotrope 70% MeOH 30% DMC | 80 | 930 | 57.4 | 42.1 | 370 | 36.7 | 30.8 | 22.8 + 9.1 DMC |
| 6 | 202 | 1.4 column of 330 cm length | 630 | 80 | 450 | 54.2 | 45.3 | 380 | 37.4 | <0.1 | 61.2 |
| 7 | 200 | 1.3[3] | 660 | 80 | 603 | 67.2 | 31.7 | 252 | 54.3 | 1.6 | 42.7 |

EGC = ethylene glycol carbonate
DMC = dimethyl carbonate
MeOH = methanol
EG = ethylene glycol
[1] and [2] In this procedure without a stripping and reinforcing part,
[1] traces of EGC and EG may still be present in the distillate and
[2] small amounts of DMC may still be present in the bottom product.
[3] Na methylate Catalyst instead of KOH

TABLE 2

| | | | | | Example 8 | | | | | |
| | | Cat. | | | Distillate[1] | | | Bottom product[2] | | |
| No. | EGC g/h | KOH g/h | EtOH g/h | Temp. °C. | g/h | % of EtOH | % of DEC | g/h | % of EG | % of EGC | % of EtOH |
| --- | --- | --- | --- | --- | --- | --- | --- | --- | --- | --- | --- |
| 8 | 104 | 2.8 | 358 | 100 | 149 | 78.7 | 20.2 | 310 | 37.7 | 26.9 | 22.2 |

EGC = ethylene glycol carbonate
DEC = diethyl carbonate
FeOH = ethanol
EG = ethylene glycol
[1] and [2] In this procedure without a stripping and reinforcing part,
[1] traces of EGC and EG may still be present in the distillate and
[2] small amounts of DEC may still be present in the bottom product.

EXAMPLE 9

44 g of EGC and 0.06 g of KOH (dissolved in 3 g of EG) were introduced per hour onto the top of a column, having a diameter of 28 mm and a length of 120 cm, which was packed with a packing of wire mesh fabric (diameter 3 mm), temperature-controlled at 80° C. and additionally equipped at the lower end with a 40 cm long stripping part heated to 100° C., and 120 g of hot MeOH vapour, at 100° C., were blown into the column from the bottom, directly above the stripping part.

When equilibrium had been established in the column, a mixture of 68.4% of MeOH and 31.6% of DMC was obtained at the top and a mixture which contained amples).

The transesterification can furthermore be controlled so that the bottom product virtually no longer contains EGC, that is to say separation of the EG/EGC azeotrope is spared (see Examples 1, 6, 9, 11, 12 and 13), which was not possible according to the prior art.

Finally, a top product which contains more DMC than corresponds to the MeOH/DMC azeotrope can be obtained (Examples 1, 4, 5, 6 and 8), and instead of MeOH, the azeotrope of MeOH and DMC can be employed, considerable additional transesterification taking place (Example 6: in addition to that metered in, about a further 1.6 mol of DMC are formed).

EXAMPLES 11-13

The educt ethylene carbonate and, separated, a solution of the catalyst KOH in ethylene glycol were metered into the upper end of a 10-tray, isothermally heated bubble tray column having a length of 68 cm and a diameter of 5 cm. At the lower end of the column, methanol in vapour form was passed in countercurrent to the stream flowing down. A Vigreux column having a length of 15 cm and a diameter of 3.5 cm was mounted as a separating unit on the top of the bubble tray column, above the metering unit. A 30 cm long separating part having a diameter of 3.5 cm, packed with 4×4 mm glass Raschig rings, was located at the lower end. The top stream was removed at the top of the Vigreux separating column, and the bottom product stream was removed at the lower end of the stripping part. The following table shows some examples of the process according to the invention. The compositions were determined after constant conditions had been established.

TABLE 3

| | | | | | Examples 11-13 | | | | | | |
|---|---|---|---|---|---|---|---|---|---|---|---|
| | | | | | Temp. °C. | Distillate[2)] | | | Bottom product[3)] | | |
| No. | EGC g/h | Cat.[1)] g/h | MeOH g/h | Temp. °C. column | stripping parts | g/h | % of MeOH | % of DMC | g/h | % of EG | % of EGC | % of MeOH |
| 11 | 200 | 1.4 | 660 | 80° C. | 80° C. | 644 | 66.0 | 33.9 | 215 | 71.4 | — | 28.0 |
| 12 | 200 | 1.4 | 660 | 80° C. | 100° C. | 680 | 68.6 | 31.3 | 179 | 84.3 | — | 15.0 |
| 13 | 202 | 1.4 | 660 | 80° C. | 120° C. | 702 | 70.2 | 29.6 | 158 | 94.5 | — | 4.8 |

EGC = ethylene glycol carbonate
DMC = dimethyl carbonate
MeOH = methanol
EG = ethylene glycol
[1)]KOH, metered as a 10% strength solution in glycol
[2)]Due to the Vigreux column mounted on the column, the distillate is practically free from EGC and EG
[3)]The bottom product is free from DMC

What is claimed is:

1. A process for the preparation of a dialkyl carbonate of the formula $$(R^1O)_2CO \quad (I)$$

in which
R[1] denotes straight-chain or branched $C_1$-$C_4$-alkyl, by transesterification of ethylene carbonate or propylene carbonate with 3-30 mols of an alcohol of the formula $$R^1OH \quad (II)$$

in which
R[1] has the above meaning, per mole of ethylene carbonate or propylene carbonate in the presence of catalysts, wherein the transesterification is carried out in a column equipped with packing or baffles at temperatures in the range of 60°-160° C. and the reactants are passed in countercurrent such that the ethylene carbonate or propylene carbonate are metered into the upper part of the column and the alcohol is metered into the lower part of the column and the catalyst is arranged as a fixed bed in the column or is also metered into the upper part of the column in solution or suspension, the dialkyl carbonate formed, if appropriate as a mixture with alcohol, being removed at the top of the column and the ethylene glycol or propylene glycol formed from the ethylene carbonate or propylene carbonate being removed at the foot of the column, if appropriate together with the catalyst.

2. The process of claim 1, wherein 4-20 mols of the alcohol are employed per mol of ethylene carbonate or propylene carbonate.

3. The process of claim 2, wherein 6-16 mols of alcohol are employed per mol of ethylene carbonate or propylene carbonate.

4. The process of claim 1, wherein the transesterification is carried out at 60°-150° C.

5. The process of claim 1, wherein the transesterification is carried out at 65°-130° C.

6. The process of claim 1, wherein the alcohol is methanol.

7. The process of claim 1, wherein the alcohol is ethanol.

8. The process of claim 1, wherein the space/time loading of the column is 0.1-3 g/ml/hour, based on the total amount of the reaction participants.

9. The process of claim 8, wherein the space/time loading is 0.2-2.5 g/ml/hour.

10. The process of claim 9, wherein the space/time loading is 0.3-2.0 g/ml/hour.

11. The process of claim 1, wherein instead of the pure alcohol, an alcohol/dialkyl carbonate mixture in which the alcohol and the dialkyl carbonate have the same alkyl radical is employed as the alcohol.

12. The process of claim 1, wherein the column has a temperature gradient with values in the stated range which increase from the top downwards.

13. The process of claim 1, wherein the middle part of the column is widened to up to four times the diameter of the remaining part of the column.

* * * * *

UNITED STATES PATENT AND TRADEMARK OFFICE
CERTIFICATE OF CORRECTION

PATENT NO. : 5,231,212

DATED : July 27, 1993

INVENTOR(S) : Buysch, et al.

It is certified that error appears in the above-identified patent and that said Letters Patent is hereby corrected as shown below:

Col. 12, line 19   Delete " claim 1 " and substitute
                   -- claim 4 --

Signed and Sealed this

First Day of November, 1994

Attest:

BRUCE LEHMAN

*Attesting Officer*         *Commissioner of Patents and Trademarks*